United States Patent [19]

Ruzicka et al.

[11] 4,006,626
[45] Feb. 8, 1977

[54] METHOD AND APPARATUS FOR EVALUATING REBOUNDING CHARACTERISTICS OF OBJECTS

[76] Inventors: Josef Ruzicka; Petr O. Ruzicka, both of 1705 Summit Ave., St. Paul, Minn. 55105

[22] Filed: Dec. 9, 1974

[21] Appl. No.: 530,991

[52] U.S. Cl. .................................. 73/13; 73/79
[51] Int. Cl.² ................................. G01N 3/52
[58] Field of Search .................. 73/12, 13, 79

[56] References Cited

UNITED STATES PATENTS

| 962,790 | 6/1910 | Shore | 73/79 |
|---|---|---|---|
| 1,441,626 | 1/1923 | Gaston | 73/79 |
| 1,490,836 | 4/1924 | Lipps | 73/79 |
| 1,504,871 | 8/1924 | Covington | 73/79 |
| 1,552,652 | 9/1925 | Sauveur | 73/79 |
| 2,333,884 | 11/1943 | Porter | 73/209 |
| 3,038,330 | 6/1962 | Criche | 73/79 |
| 3,482,430 | 12/1969 | Percarpio et al. | 73/12 |
| 3,496,765 | 2/1970 | Rathmell | 73/79 |

Primary Examiner—Charles A. Ruehl
Attorney, Agent, or Firm—James R. Haller; Warren A. Sturm

[57] ABSTRACT

A performance method and apparatus for evaluating the bouncing or rebounding characteristics of objects such as balls used in games, and for evaluating the energy-absorbing and surface characteristics of playing surfaces of games.

9 Claims, 14 Drawing Figures

METHOD AND APPARATUS FOR EVALUATING REBOUNDING CHARACTERISTICS OF OBJECTS

BACKGROUND OF THE INVENTION

Individual or team games involving the use of a ball or like object which rebounds from a ball-impacting surface such as a floor, paddle or racket, have rapidly risen in popularity, and many of such games have been elevated from a relatively informal status to the level of national and international competition. Examples of such games are lawn tennis, table tennis and handball. The rules of play governing games of this type have been carefully developed, but few performance standards governing the equipment for such games have been devised.

In the game of handball, for example, the United States Handball Association (U.S.H.A.) rules describe the handball as being of black rubber with a given diameter and weight, but all that is said about ball performance is that the ball must rebound in a non-erratic fashion from 42 to 48 inches when dropped from a height of 70 inches at 68° F. The rules do not specify the energy absorbing characteristics of the surface upon which the ball is dropped, nor do they take into account the variations in symmetry and homogeneity which may give rise to erratic rebounding of the ball from playing surfaces.

The 1974 Rules of Lawn Tennis Play (International Lawn Tennis Federation), as another example, specify that a tennis ball must have a given weight and given dimensions, a particular deformation under load taken 3 axes, and must rebound from 53 to 58 inches when dropped from a height of 100 inches upon a concrete base. Other then the rebound height test, there is no practical test given for insuring the symmetry and homogeneity of the ball so that the ball will not bounce erratically upon a playing surface.

As yet another example, the Rules of United States Table Tennis Association (U.S.T.T.A.) specify that a table tennis ball (a Ping-Pong ball) shall have a given diameter and weight, that it must be spherical and made of celluloid or similar plastic, and that it must rebound within a given range when dropped on to a steel plate. No account taken of the symmetry or homogeneity of the ball. The latter item is of great importance in table tennis because of the spin often imparted to the ball in play and because of the relatively heavy seams between halves of the ball.

The same surprising lack of extrinsic performance standards applies to surfaces upon which games of the above nature are played, and to the rackets or paddles, or the like which are used. When a ball, for example a handball, strikes a playing surface such as the floor, the rebounding of the ball is dependent upon the amount of kinetic energy which the ball loses as it strikes and rebounds from the floor. If the floor is particularly capable of absorbing energy (i.e., if it is made of a deformable material such as soft rubber or the like), the ball will rebound to a lesser degree than it would were the floor made of an extremely, immovable material such as concrete or steel. Similarly, it is evident that a ball (for example, a table tennis ball) will receive different amounts of momentum when struck by a paddle of resilient material such as sponge rubber and when struck by a paddle of unyielding material such as hardwood.

The variances between different brands and grades of balls used in any given sport can often be quite large. Different brands of table tennis balls, for example, have different seams which can greatly effect the performance of the balls. The performance of inflated balls, such as racket balls, tennis balls, basket balls, and the like is greatly dependent upon the internal pressure of the ball. The internal pressure of tennis balls, for example, tends to decrease during storage. The performance of paddles such as those used in table tennis is likely to vary greatly from one brand of paddle to another, and we have found that the type of surface covering (e.g., rubber, sandpaper, etc) which is employed on table tennis paddles is of great importance of stringed rackets, such as tennis rackets, depends greatly upon string tension.

Because of the increasing popularity of games such as those mentioned above, there is a need for some means of standardizing playing equipment, particularly ball and ball rebounding surfaces, so that fairness may be assured between players using different courts or playing surfaces, and different balls. Moreover, some means is needed to measure the actual performance of balls used in such games, and playing surfaces so that the erratic rebounding of balls due to deviations in symmetry and homogeneity can be greatly reduced or eliminated.

SUMMARY OF THE INVENTION

The present invention provides a method and apparatus for testing the performance characteristics of balls and of ball-impacting surfaces upon which such balls rebound. The apparatus includes means for dropping a ball from a predetermined height substantially without imparting spin to the ball, a ball-impacting substrate positioned beneath the ball dropping means and having predetermined rebound characteristics, means defining a vertical unobstructed pathway for the ball to travel in its fall from the ball dropping means to the substrate, and a scale for measuring the vertical rebound distance of the ball from the substrate. The scale includes at least two sets of generally vertical spaced ruled marks with corresponding marks in each set being horizontally spaced from one another. Each set of ruled marks lie along and to the side of the path traveled by the ball in its free fall to the substrate so that a viewer may align two identical marks with the top or bottom of the ball as the latter reaches the zenith of its rebound.

In a preferred embodiment, the substrate is in the form of a target having an impact portion vertically aligned with the ball releasing means and a series of concentric rings spaced about the impact portion. The rings may include indicia indicating their respective radial distances from the center of the substrate. The apparatus, together with the substrate as thus described, provide a measure of the "balance" of the ball being tested. Although a test ball will rebound first from the impact portion of the substrate, its next (second bounce) contact with the substrate may be at a point spaced from this portion. The horizontal distance separating the first and second bounce points provides an indication of the "balance" of the ball in that a ball which is perfectly spherical and homogeneous will continue to bounce substantially along the vertical path between the ball release means and the substrate, whereas a ball which is out of round or non-homogeneous will tend to bounce outwardly from the vertical path.

By "ball", as used herein, reference is made particularly to the common, spherical or spheroidal balls used in such games as handball, tennis, basketball, and the like. This term also includes, however, generally rounded game projectiles such as shuttlecocks and footballs. By ball, reference is also made to game projectiles such as golf balls which are only grossly spherical and which have a number of small surface dents. Despite the surface dents, golf balls may be adequately tested for rebound height and balance with the apparatus and method of the present invention, and it has been found that the dents do not cause erratic rebounding of the ball to any appreciable extent. The term ball also includes test projectiles of various materials and products to be tested, such as experimentally compounded rubbers and plastics.

DESCRIPTION OF THE DRAWING

FIG. 11 A and B are side and top schematic representations of the rebound measuring system of the present invention; and FIG. 12 A and B are side and top schematic representations of the balance measuring system of the present invention.

BRIEF DESCRIPTION OF THE PREFERRED EMBODIMENT

Figures 1, 2, 3, 4:
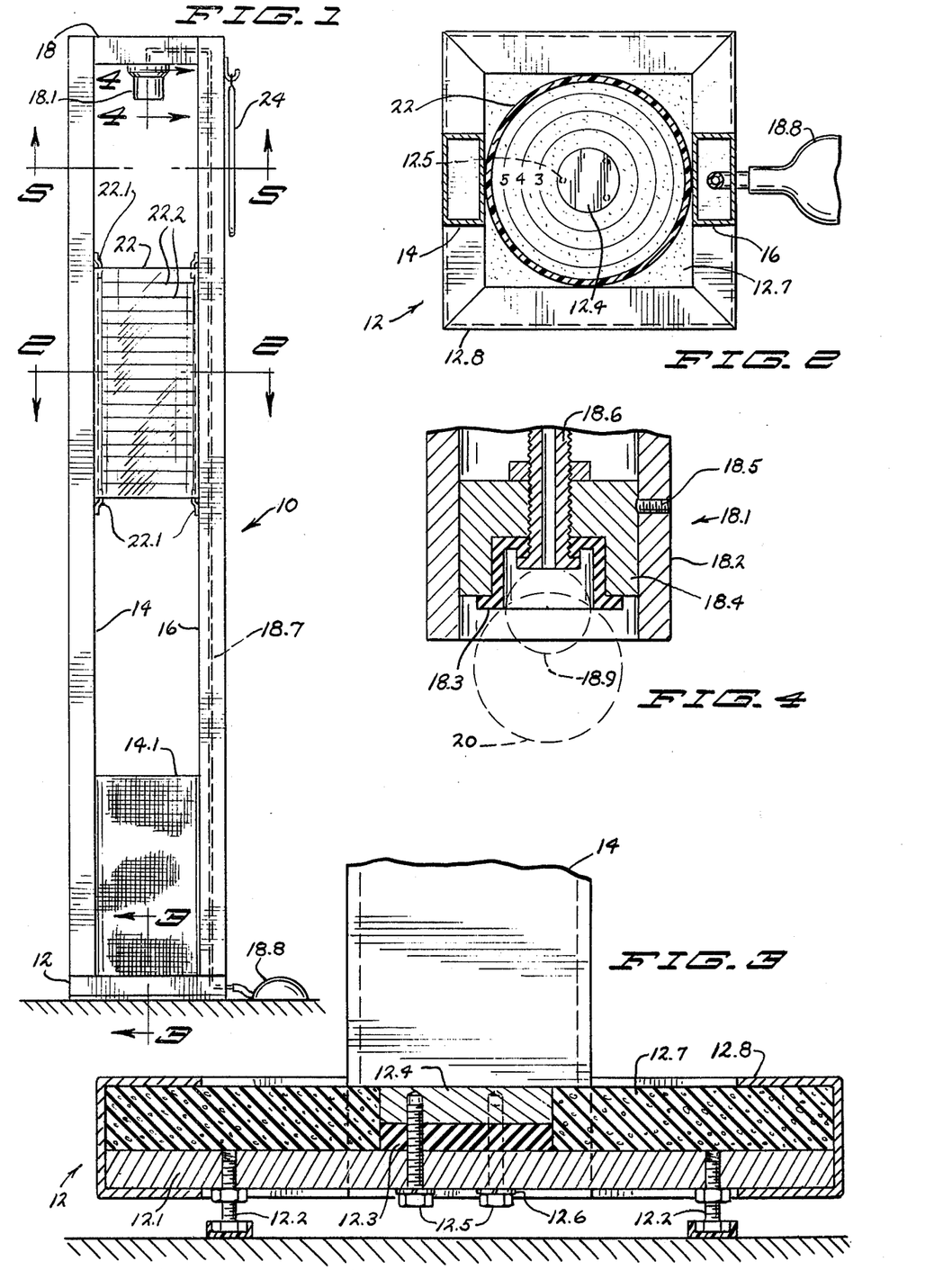
FIG. 1 is a front view of an apparatus of the invention useful in testing the performance characteristics of a handball.
FIG. 2 is a cross sectional view taken along line 2—2 of FIG. 1.
FIG. 3 is a cross sectional view, partially broken away, taken along line 3—3 of FIG. 1.
FIG. 4 is a cross sectional view taken along line 4—4 of FIG. 1.
Figure 5:
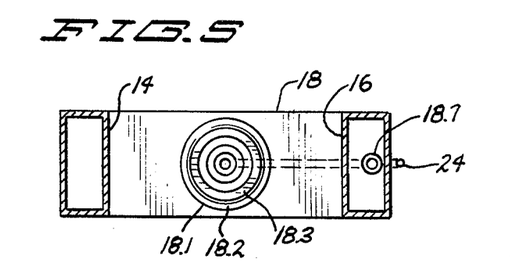
FIG. 5 is a cross sectional view taken along line 5—5 of FIG. 1.

The apparatus of the invention as depicted in FIGS. 1–5 is designated generally as 10 in FIG. 1 and includes a base 12 of generally rectangular cross section, a pair of upright braces 14, 16 joined at their lower ends to the base, and a cross bar 18 joining the upper ends of the braces, the braces holding the cross bar in generally vertical alignment with the base and being spaced apart a sufficient distance to enable a ball to be dropped from a point near the cross bar and to pass between the braces toward the base.

The base includes a generally horizontal base plate 12.1 of heavy gage steel or like material, as shown best in FIG. 3. Leveling screws 12.2 are threaded into threaded holes in the base so that the base may be precisely adjusted to lie in a horizontal plane. Resting on the base is a pad 12.3 of sponge rubber, foamed plastic, or other compressible material. Carried by the resilient pad 12.3 is a ball impact substrate such as bounce plate 12.4, which may be of steel or other appropriate material having a smooth upper surface. Three hold-down screws 12.5 are passed upwardly through holes in the base plate and resilient pad and are threaded from beneath into threaded holes in the bounce plate 12.4. The hold-down screws 12.5 serve to squeeze together the base plate and bounce plate, compressing the resilient pad 12.3 to vary the rigidity or energy absorbtion characteristics of the bounce plate when a ball strikes the latter, as will be subsequently explained in greater detail. The hold-down screws 12.5 are spaced circumferentially about the periphery of the bounce plate 12.4, as shown best in FIG. 2.

The bounce plate and pad, as noted, are centrally positioned with respect to the base plate 12.1, and may have a diameter of less than half that of the base plate. The remainder of the base plate is overlaid with a layer 12.7 of sponge rubber or the like having any upper surface which lies in approximately the same plane as that of the bounce plate 12.4. The periphery of the base plate and sponge rubber layer is enclosed by a sheet metal frame 12.8 which is generally C-shaped in cross section, as shown best in FIG. 3. Upon the upper surface of the exposed foam rubber layer 12.7 may be scribed a series of concentric circles radially spaced a given distance from one another, as shown in FIG. 2.

The vertical braces 14, 16 are bolted or otherwise rigidly connected at their lower ends to the base plate 12.1, since it is important that the cross bar 18 at the top of the braces be vertically aligned with the bounce plate 12.4 at the bottom of the apparatus. A circular screen 14.1 of wire or fabric may be rested upon the base 12 between the braces to retard the escape of balls which bounce from the bounce plate 12.4.

The cross bar 18 is provided with a downwardly-open ball release shown best in FIG. 4. The ball release includes cylindrical metal sleeve 18.2 bolted to the cross bar and including therewithin a downwardly open, generally cup-shaped ball holder 18.3 seated in an adjustment block 18.4. The adjustment block centers the ball holder within the sleeve 18.2, and is movable vertically within the sleeve to adjust the height of the ball holder by means of a set screw 18.5. A vacuum tube 18.6 is threaded downwardly through the adjustment block 18.4 and ball holder 18.3 to communicate with the cup-shaped interior to the ball holder. To the vacuum tube 18.6 is attached an air line 18.7 which passes through the interior of the cross bar 18 and brace 16 to emerge at the base 12. A foot-operated squeeze bulb 18.8 is connected to the vacuum line 18.7 at its lower end adjacent the base for the purpose of providing a vacuum within the vacuum line and for releasing the vacuum. The center of the cup-shaped ball holder 18.3 is precisely aligned vertically with the center of the rebound plate 12.4 at the base of the apparatus so that when a ball 20 (shown in dotted lines in FIG. 4) is released from the holder, it will drop downwardly between the braces 14, 16 to strike the bounce plate 12.4 in its center.

A scale is provided along the path taken by a ball during its fall from the ball release to the bounce plate, the scale having at least two sets of vertically-spaced ruled marks with the marks of one set being spaced horizontally from the marks of the other set. In its preferred embodiment, the scale takes the form of a hollow plastic cylinder 22 of a diameter of, for example, 8 inches, permitting it to fit between the braces 14, 16 as depicted in FIGS. 1 and 2. Mounting brackets 22.1 releasably hold the cylinder 22 in a position coaxial with the fall path of a ball from the ball releasing device to the bounce plate. The ruled marks 22.2 may be scribed about the circumference of the cylinder so that one may align a given rule mark on one side of the cylinder with the corresponding rule mark on the other side of the cylinder and then also align the two marks with the top of a ball bouncing upwardly from the bounce plate 12.4.

In the embodiment depicted in FIGS. 1–5, the device is employed for testing the performance characteristics of a handball, racquet ball, golf ball, etc. The bounce plate 12.4 is of heavy steel having a machined, polished upper surface, and the cylindrical scale 22 is positioned so that a mark midway along its length is spaced (for handball) approximately 48 inches above the bounce plate. A thermometer 24 is attached to the apparatus (FIGS. 1 and 5) to measure the ambient temperature, since the performance of a ball is temperature sensitive, as will be described in more detail below. It will be understood that the base 12 may be removed so that the apparatus may be used to measure characteristics of other substrates such as paddles, floors, etc.

Figure 8:
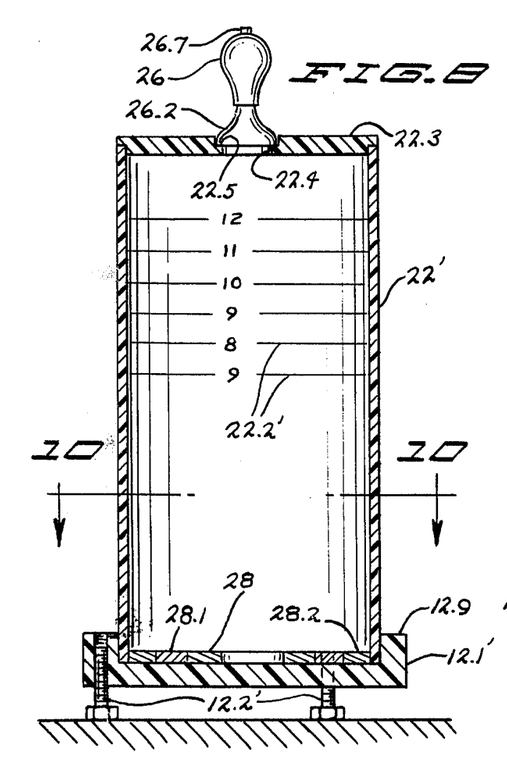
FIG. 8 is a front view, in cross section of an apparatus of the invention useful in measuring the performance characteristics of table tennis balls.
Figure 9:
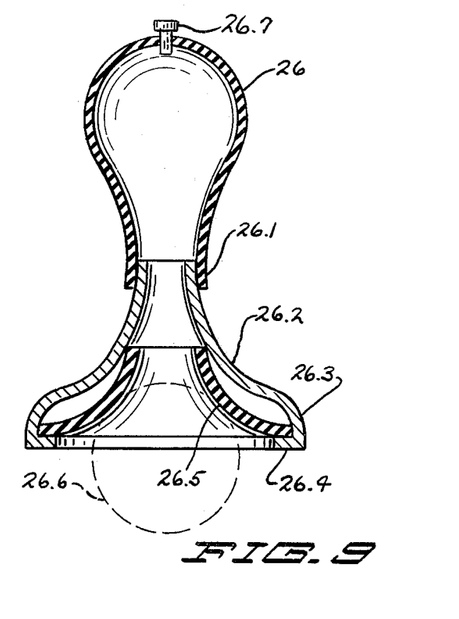
FIG. 9 is a cross sectional view of a ball release used in the apparatus of FIG. 8.
Figure 10:
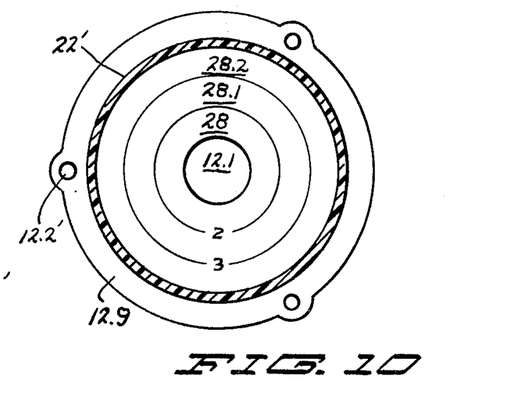
FIG. 10 is a cross sectional view taken along line 10—10 of FIG. 8.

FIGS. 8–10 show another embodiment of the invention which may be employed in testing the performance characteristics of table tennis balls. In this embodiment, the base 12.1' is generally circular in cross section as shown in FIG. 10, and the upper surface of the base is adapted to function as the bounce plate 12.4 in the apparatus of FIGS. 1–5. The base 12.1' may be leveled by means of leveling screws 12.2'. The base 12.1' includes a turned up lip 12.9 about its periphery. A scale carried by a hollow, transparent plastic cylinder 22 of 6 inch diameter and 13½ inches in length fits against the base 12.1' at its lower end and is centered in the base by means of the upwardly turned lip 12.9. The scale, which includes at least two sets of vertically-spaced ruled marks, may take the form of circumferential marks 22.2' so that an observer may look through the plastic cylinder align the marks on one side thereof with the corresponding marks on the other side. At its upper end, the cylinder is provided with a cover 22.3 having a central bore 22.4, the cover being counter-bored from above to provide an upwardly facing shoulder 22.5 about the periphery of the bore.

A flexible rubber suction bulb 26 (FIG. 9) is attached at its lower, nozzle end 26.1 to the narrow open end of a bell or cup 26.2 of steel or other hard material, the wide mouth 26.3 of the bell opening downwardly and having a peripherial lip 26.4 which fits within the counterbored opening in the cover 22.3 of the device of FIG. 8. The lip seats upon the upwardly facing ledge 22.5 of the cover. Held within the bell 26.2 is a rubber insert 26.5 of generally conical shape with its side walls flaring downwardly and outwardly to provide a vacuum seat or seal for a table tennis ball. In FIG. 9, the position of a vacuum-seated ball is shown in phantom lines as 26.6. The bulb 26 is provided at its upper, closed end with a bleeder valve such as needle valve 26.7. The valve permits air to enter the bulb at a gradual rate to neutralize the vacuum produced therein when the bulb is squeezed and then released with a ball seated in the rubber insert.

The hollow, transparent cylinder 22' (FIG. 8) is purposefully made easily removable from the base plate 12.1' so that the cylinder may be placed upon the playing surface of a Ping-Pong table, or paddle, and the latter surfaces may be then used to measure rebound, as will be explained in greater detail below.

Arranged concentrically upon the upper surface of the base plate 12.1' are rings of different material, each preferably having a flat, upper surface and each having a characteristic sound when struck by a ball. For example, the inner most ring 28 may be of paper so as to yield a crackling sound when struck by a ball. The middle circle 28.1 may be of hardwood, yielding a slight tone when struck, and the outer circle 28.2 may be of foam rubber so as to yield substantially no sound at all when struck. By listening to the sound made by the ball striking one of the rings on second bounce, an operator can tell which of the rings was struck and can thus determine the gross distance of the impact of the ball, on second bounce, from the center of the base plate. It will be noted that the innermost ring 28 terminates short of the center of the base plate so that the ball drops onto the base plate itself. If desired, the thus described "rings" may be provided with appropriate electrical connections so as to read out the ring which is struck, as by causing a colored light to light upon a read-out board, etc.

In another embodiment, a "magic slate" is substituted for the rings 28-28.2 such that the impact of a ball, on second bounce, against the magic slate material causes a visible imprint to be made on the slate, thus recording the position of the impact. Magic slate materials are well known, and generally comprise a substrate of deformable, waxy material such as wax, having an overlayer of a normally translucent sheet of plastic which becomes transparent when pressed against and wetted by the waxy substrate.

In yet another embodiment, the concentric rings may be replaced by a surface to which the ball, on second bounce, clings when it impacts, such as a surface of sticky adhesive. Or, the surface replacing the concentric rings may be dusted with a powder or other material which is disrupted when struck by a ball so as to leave a visible track. One skilled in the art will be able to visualize other appropriate substrates for providing an indication or record of the point at which the ball, on second bounce, strikes the substrate.

Figure 6:
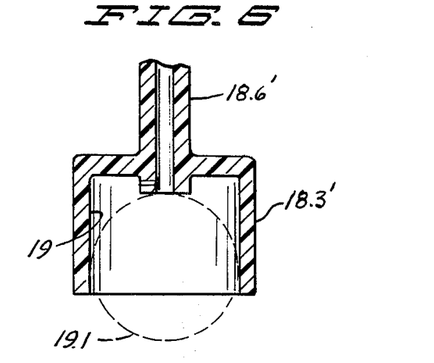
FIGS. 6 and 7 illustrate different embodiments of a ball release depicted in FIG. 4.
Figure 7:
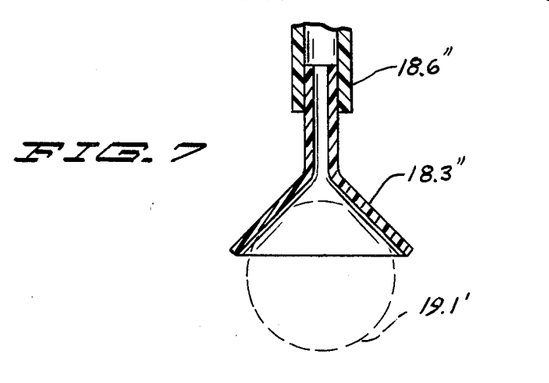

FIGS. 6 and 7 depict ball release devices which are slightly modified from the device of FIG. 4. In FIG. 6, the ball holder 18.3' has generally cylindrical, vertical inner wall surfaces 19 which very gently engage the ball (designated 19.1 and shown in phantom lines). This type of ball holder is useful for holding and releasing large balls such as volley balls and basketballs, or balls having uneven or fuzzy surfaces, such as tennis balls, baseballs, or golf balls. The cylindrical inner wall surfaces 19 extend vertically a sufficient distance so as to gently engage the largest diameter of the ball when the ball is in its held position. As in the device in FIG. 4 a vacuum is drawn through the line 18.6' to hold the ball in place, and the engagement between the ball and the cylindrical walls of the ball holder is such as to only very slightly restrain, with aid of the vacuum, the ball and the holder. When the vacuum is released, the weight of the ball preferably overcomes the mechanical engagement between it and the side walls of the holder so as to release from the holder. It may be necessary, in some instances, to apply slight pressure to the top of the ball to urge it to fall. The cylindrical walls 19 need not be perpendicular, but may diverge outwardly slightly so that as the ball is released, it disengages from all points of gentle contact with the cylindrical wall substantially simultaneously. In this manner, substantially no spin is imparted to the ball.

In FIG. 7, the walls of the holder 18.3'' are flared outwardly at angles of about 45° to the vertical, and the ball (depicted in FIG. 7 in phantom lines as 19.1′) is held in its vacuum seat against the outwardly flaring inner surface of the holder. Referring again to FIG. 4, a smaller ball (depicted in phantom lines as 18.9) is shown in its seating engagement against the lower surface of the vacuum tube 18.6 itself, the lower surface of the vacuum tube being substantially horizontal and with the vertical walls of the holder 18.3 being spaced outwardly slightly from the ball. In comparing FIGS. 4, 6 and 7, it will be noted that the points of contact forming the vacuum seat in which the ball is held may be substantially vertical (FIG. 6) or may approach the horizontal (FIG. 4); that is, the tangent of the ball representing its seat against the ball holder may range from vertical through any acute angle approaching the horizontal.

Figure 11:
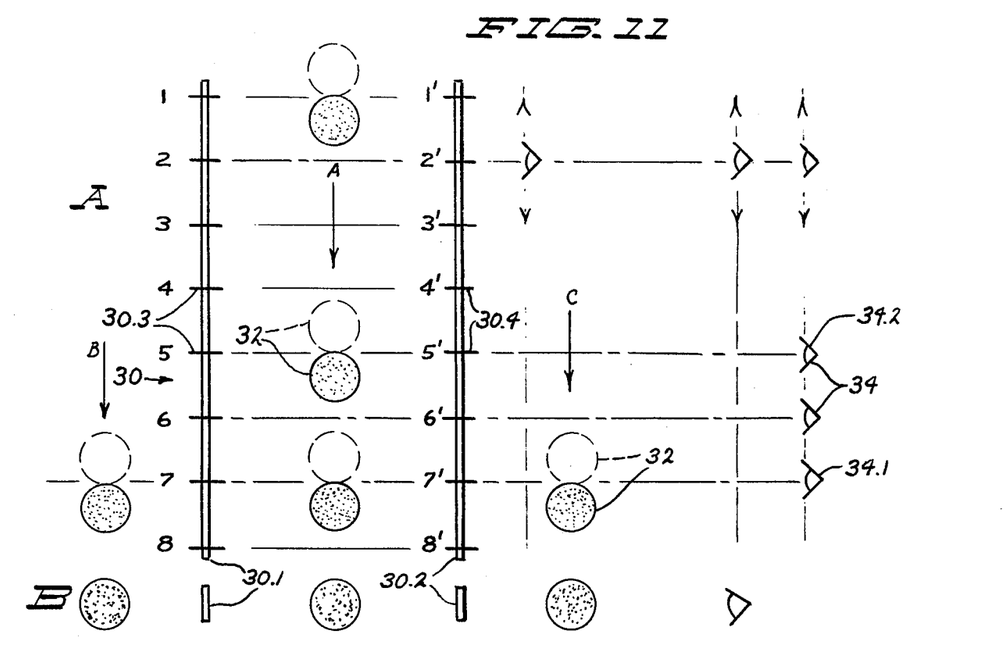

FIG. 11 depicts the manner in which the rebound height of the ball may be read. A scale, designated generally 30, includes at least two sets of ruled marks 30.1, 30.2 which are spaced vertically with the ruled marks 30.3 of one set being spaced horizontally from and in horizontal alignment with the corresponding ruled marks 30.4 of the other set. The sets of ruled marks, for example, correspond to the marks 22.2 carried circumferentially of the hollow plastic cylinder 22 in FIG. 1 so that one set of the ruled marks corresponds to those lines on the cylinder nearest the observer and the other set of ruled marks correspond to those on the opposite side of the cylinder. The apparatus includes a pathway of reasonably great breadth through which the ball (depicted as 32 in FIG. 11) drops in its path from the ball release means to the substrate or bounce plate at the bottom of the apparatus. In FIG. 11, we show that the ball may be dropped between the sets of ruled marks (indicated by arrow A) or may be dropped on either side of the sets of ruled marks (indicated by arrows B and C respectively). Accuracy in measuring the rebound height of a ball is assured by aligning the eye (generally, 34) of the observer horizontally with identical marks in each set of ruled marks before the ball is initially dropped. If the rebound height of the ball is greater of less than that of the line joining the eye of the operator with identical marks in each set of ruled marks, then the eye of the operator is raised or lowered to the approximate height of the rebound and the ball is dropped again. Since the rebound height of a number of different balls is not likely to vary greatly, once an assumed average rebound height is determined, the operator may initially sight across the marks at the average height and then quickly adjust his eyes upwardly or downwardly according to the rebound height of a particular ball being tested. In this manner, the rebound height of a ball may be easily determined, and the horizontal line-of-sight provided by the aligned ruled marks prevents parallax readings and lends accuracy to the readings.

For example, assume that the eye is initially positioned at the lower level in FIG. 11 (designated 34.1). In its rebound, assume that the ball rises to the apparent level shown by the ruled marks labeled 5, 5′. For the next dropping sequence, the operator will move his eye upwardly to the position designated 34.2 so that a precise measurement of the rebound height can be obtained.

It is preferred that the rebound height of the ball be measured by observing the top of the ball, that is, the sighting desirably is made across two points representing aligned, identical marks on the ruled sets of marks, and a third point representing the top surface of the ball at the zenith of its rebound. Alternatively, however, readings may be taken at the bottom off the ball (as shown in phantom lines in FIG. 11), or at the maximum diameter of the ball, or any other convenient point.

The balance of a ball is a function of its symmetry and homogeneity and is a measure of how erratically a ball rebounds from a playing surface. The balance of a ball tested with the apparatus of the present invention may be determined by viewing how erratically the ball rebounds after it has been dropped onto a selected surface. Since the ball release of the present invention permits a ball to drop substantially without spin, the erratic behavior of a seamed ball on rebound will depend to a large extent upon the original orientation of the ball in the holder. For example, table tennis balls ordinarily are made with a seam about their diameter, and the balance of the ball as measured with the apparatus of our invention will depend upon the orientation of the ball as it strikes a surface. For example, if the seam is considered the equator of the ball, and the ball is dropped so that is impacts at one of its poles upon a substrate, the ball is unlikely to rebound very erratically. On the other hand, if the ball is so held as to impact at a point near its equator, the rebound is far more likely to be erratic. Testing of the balance of a ball, accordingly, requires the ball to be dropped from several orientations so as to obtain an average and a maximum figure for erratic rebounding.

Figure 12:
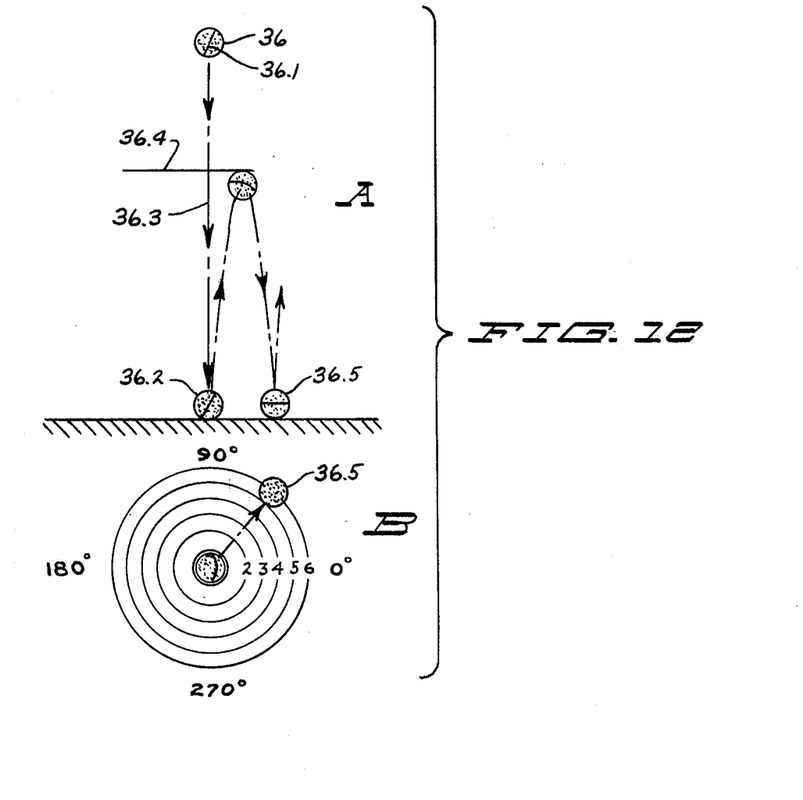

FIG. 12 schematically depicts side and top views of the rebounding of a poorly balanced ball which, for this example, may be a table tennis ball. The ball is depicted at 36 in its original orientation in the ball holder, the equatorial plane of the ball being designated 36.1 and being oriented slightly away from the vertical. The ball strikes the substrate at 36.2 and because of the heaviness of the seam or other imbalance-producing feature, it rebounds slightly to one side of the path 36.3 and reaches a rebound zenith designated 36.4. On its second bounce, the ball impacts at a point spaced radially away from the center of the intersection of the drop path 36.3 and the substrate, and the magnitude of this radial distance provides an indication of the balance of the ball. As noted above, to obtain a realistic indication of ball performance, the ball should be dropped several times in several different orientations. The second bounce impact of the ball is designated 36.5, and it will be noted from FIG. 12B that the ball has not bounced directly to the right (toward the 0° mark) as expected, but rather bounced unexpectedly at an angle of approximately 45°.

The apparatuses and methods of the present invention, although preferably used with a substrate having given rebounding qualities for testing the rebound height and balance of balls, may be employed as well on a playing surface, such as a handball or tennis court, to determine the rebound characteristics of that surface. For example, the apparatus depicted in FIG. 1 was employed to test the rebound and balance characteristics of a number of handballs, and a similar apparatus was employed to test the rebound characteristics of a handball court at the St. Paul Athletic Club, St. Paul, Minnesota. A group of 20 handballs were tested with the device of FIGS. 1–5. The drop distance was set at 70 inches, and a heavy steel plate with a smooth, horizontal upper surface was employed as the substrate. The test temperature in each case was 68° F. The tested handballs were Spalding "Red Label ACE" handballs. The 100 tests produced an average rebound height of 48½ inches, and individual tests yielded minimum height of 47¼ inches and a maximum height of 50 inches.

The balance, that is, the distance from the center of the rebound base to the point of impact of the ball on second bounce, was also measured. Results were reported to the nearest ¼ inch. The average distance in the 100 tests was 1.85 inches, and the individual measurements varied from a distance of 0 inches to a distance of over 4 inches.

The handball court floor was measured at 15 points spaced across the surface of the floor. The handball used in the test was calibrated as to rebound height using the apparatus of FIGS. 1-5 before and after the rebound characteristics of each floor position were measured. Each position on the floor was measured using 3 drops, and the average thereof was taken as the rebound height for that position. Rebound height varied across the floor from a low of 49⅜ inches, to a high of 50¼ inches, indicating that the rebound characteristics of the floor were quite uniform. The average rebound distance from the floor was found to ¼ inch higher than the average rebound distance using the apparatus of FIGS. 1-5.

Our tests indicated that the average rebound heights of new handballs of the type described were slightly greater than the upper limit of the range given in the U.S.H.A. Rules as set out above. As a result, and in view of our balance tests, we have suggested the following handball standards be set:

Temperature 68° F. ± 1° F.
Rebound From 70 inches 49 ± 1½ inches
Balance Less than 3½ inches
Special Conditions
    5 tests shall be obtained for each handball, and the results for each test shall be within the ranges for rebound height and balance set out above.

The apparatus of the invention may also be employed to measure the rebound characteristics of paddles or racquets. In one test, for example, the apparatus of FIG. 8 was employed to test table tennis balls, paddles and tables. The table tennis balls were new T.S.P. Astoll balls, and the results of rebound height and balance tests of twelve of these balls, each ball dropped five times, are reported below. The impact substrate was of flat, rigid, clear plastic, the drop height was 12 inches, and the tests were conducted at 70° F. and 25% relative humidity.

Rebound height range: 9 11/16 to 9¾ inches
Balance range: 0 to 1.5 inches

The base 12.1' of the apparatus of FIG. 8 was removed, and the cylinder 22' was placed on the hitting surfaces of table tennis paddles for testing the rebound heights of different types of paddles. The drop height remained 12 inches, and each test consisted of five drops.

|  | Rebound Height, Inches | |
|---|---|---|
|  | Minimum | Maximum |
| Paddle 1, front side | 7 3/16 | 7 1/4 |
| Paddle 2, front side | 2 5/8 | 2 7/8 |
| Paddle 2, rear side | 7 3/8 | 7 1/2 |
| Paddle 3, front side | 6 7/8 | 6 15/16 |
| Paddle 3, rear side | 6 7/8 | 6 15/16 |

The cylinder was then placed at seven different positions on three table tennis tables, and the rebound height tests were repeated to test the rebound characteristics of the tables:

|  | Rebound Height, Inches | |
|---|---|---|
|  | Minimum | Maximum |
| Table 1 | 9 7/16 | 9 1/2 |
| Table 2 | 9 7/16 | 9 1/2 |
| Table 3 | 9 9/16 | 9 1/2 |

The temperature of the ball being tested has been found to have a significant, but predictable, effect upon rebound height. For example, we have found that the rebound height of balls used in the game of handball varies substantially linearly with the temperature of the ball being tested. From data taken at different temperatures in the range of 65° to 83° F., we have found the rebound height of the ball to increase by 0.15 inches on the average, per 1° F. rise in temperature. Since temperature greatly effects the internal pressure of gas-filled balls such as tennis balls, volley balls, and the like, it is desirable that such balls be tested at a given, preselected temperature such as 68° F. The deviations in rebound height due to testing of such balls at slightly different temperatures can be compensated for by applying a correction factor.

Referring again to FIG. 3, the pad 12.3 upon which the bounce plate 12.4 rests in the apparatus of FIGS. 1—5 is adapted to absorb energy from a ball bounced against the plate. The hold-down screws 12.5 control the resiliency and energy-absorbing characteristics of the pad 12.3 so that the energy absorbed as a ball strikes the bounce plate 12.4 can be varied at will. Three such hold-down screws 12.5 are employed to permit the bounce plate 12.4 to be leveled and to vary the height of the pad 12.3. If desired, of course, a single, central hold-down screw could be provided for this purpose.

In the experiment referred to above with reference to on similar to that apparatus of FIG. 1 (without base plate and substrate) was employed to measure the rebound height of handballs from a particular handball court floor. After an average rebound height had been determined, the same handballs were employed to calibrate the tester of FIG. 1 by carefully adjusting the hold-down screws 12.5 at the base until the same average rebound height was obtained, care being taken to maintain the bounce plate 12.4 in a precisely horizontal plane. The floor of a tennis court was also tested in this fashion.

The apparatus of the present invention, ad described above, may also be employed as a game or learning device for teaching children mensuration or for purely play purposes. For example, the cover 22.3 of the apparatus of FIG. 8 may be removed, and children may throw Ping-Pong balls from a distance into the cylinder 22', with one child throwing the Ping-Pong balls and the other child measuring the height to which they rebound.

While we have described a preferred embodiment of the present invention, it should be understood that various changes, adaptations, and modifications may be made therein without departing from the spirit of the invention and the scope of the appended claims.

What is claimed:

1. Apparatus for testing performance characteristics of balls and ball-impacting surfaces comprising a horizontal substrate, ball releasing means supported above and in vertical alignment with the substrate and capable of releasing a ball substantially without spin, the ball releasing means comprising a downwardly open holder having inner walls parallel to or at an acute angle with the vertical, the inner surface of the wall providing a peripheral vacuum seat against which the ball is seated, means providing a pressure differential between the top and bottom of the ball to hold the ball in seating engagement therein, and means for changing said pressure differential to permit the ball to drop from the holder; means providing a free-fall path for the ball from the release means to the substrate; and a scale for measuring rebound height, the scale comprising at least two sets of vertically spaced, height-indicating rule marks with the marks of one set spaced from and horizontally aligned with identical marks of the other set, the sets of rule marks being so positioned with respect to the free-fall path of the ball as to permit alignment of identical marks in each set with the ball as the latter reaches its maximum rebound height.

2. Apparatus for testing performance characteristics of a ball and ball impacting surfaces, comprising a substrate upon which a ball is dropped and a scale for measuring the rebound height of the ball, the apparatus providing an unobstructed free-fall path for the ball having a width of at least one and one-half ball diameters, and the apparatus including ball releasing means positioned above and in vertical alignment with the substrate, the ball releasing means including means defining a horizontal, circular seat, and means for creating an air pressure differential across the ball of sufficient magnitude to itself retain the ball in said seat at an elevated, predetermined position above the substrate, and means for changing the air pressure differential across the ball to permit the latter to fall under its own weight onto the substrate.

3. The apparatus of claim 2 in which said means creating the pressure differential comprises means for producing a vacuum above the circular seat.

4. Apparatus for testing the performance characteristics of balls and ball impacting surfaces, comprising a horizontal ball impacting substrate and ball releasing means positioned above and in vertical alignment with the substrate to permit a ball to drop, substantially without spin, onto a predetermined point on the upper surface of the substrate, the apparatus including means for measuring the distance between the predetermined point on the substrate and a second point of impact of the ball on the substrate corresponding to its second bounce to provide a measurement of the balance of the ball, the distance measuring means comprising a series of radially spaced concentric rings on the substrate about said predetermined point, said rings being of material producing a visible mark when struck by a ball.

5. Apparatus for testing the performance characteristics of balls and ball impacting surfaces, comprising a horizontal ball impacting substrate and ball releasing means positioned above and in vertical alignment with the substrate to permit a ball to drop, substantially without spin, onto a predetermined point on the upper surface of the substrate, the apparatus including means for measuring the distance between the predetermined point on the substrate and second point of impact of the ball on the substrate corresponding to its second bounce, to provide a measurement of the balance of the ball, the upper surface of the substrate surrounding but spaced from the predetermined point being of a material to which the ball adheres on its second bounce.

6. Method of measuring the rebound characteristics of a ball or ball-impacting surface, comprising
   a. providing a horizontal substrate comprising a horizontal bounce plate, a resilient bed supporting the bounce plate, and means for changing the resiliency of the bed, and a ball release positioned above and vertically aligned with the substrate to drop the ball substantially without spin toward the substrate;
   b. providing a vertical scale including at least two sets of vertically spaced, ruled marks, the marks of one set being spaced from and horizontally aligned with corresponding marks of the other set, at least two of the horizontally spaced sets of marks being aligned with the path of travel of the ball as the latter is dropped from the ball release to the substrate, the horizontally aligned marks of each set serving to align the eye of an operator in horizontal plane thereacross; and
   c. dropping a ball from the ball release onto the substrate, and horizontally viewing, with the aid of the sets of marks, the height to which the ball rebounds.

7. In the method of measuring the balance of a ball which comprises dropping the ball in a vertical path from a predetermined height onto a horizontal ball-impacting surface, noting the impact point of the ball on its second bounce, and measuring the horizontal distance from said vertical path to the point of impact of the ball on its second bounce, the improvement comprising providing the ball impacting surface with a horizontal substrate surrounding but spaced from the vertical path, the substrate including separate means for automatically indicating the point of second impact of the ball corresponding to its second bounce other than by momentary observation of the latter point of impact.

8. Method for dropping a ball upon a substrate substantially without imparting spin to the ball which comprises:
   a. providing a downwardly open ball release having a seat engaging the ball in a substantially airtight manner, the locus of points of engagement between the ball and seat forming a circle lying in a horizontal plane and having a diameter less than that of the ball;
   b. imparting an air pressure differential across the ball in which the air pressure above the ball is less than that below the ball said differential itself holding the ball to the ball release; and
   c. neutralizing the air pressure differential to cause the ball to fall directly downwardly under its own weight substantially without having spin imparted to it by the ball release.

9. Apparatus for testing performance characteristics of balls and ball-impacting surfaces comprising a horizontal substrate, ball releasing means supported above and in vertical alignment with the substrate and capable of releasing a ball substantially without spin; means providing a free fall path for the ball from the release means to the substrate, and a scale for measuring rebound height, the scale comprising at least two sets of vertically spaced rule marks with the marks of one set spaced from and horizontally aligned with identical marks of the other set, the sets of rule marks being so positioned with respect to the free fall path of the ball as to permit alignment of identical marks in each set with the ball during rebound of the latter, said substrate comprising a horizontal bounce plate, a resilient bed supporting the bounce plate, and means for changing the resiliency of the bed.

* * * * *